(12) United States Patent
Hitt et al.

(10) Patent No.: US 7,333,896 B2
(45) Date of Patent: Feb. 19, 2008

(54) QUALITY ASSURANCE/QUALITY CONTROL FOR HIGH THROUGHPUT BIOASSAY PROCESS

(75) Inventors: Ben A. Hitt, Gaithersburg, MD (US); Peter J. Levine, Potomac, MD (US); Emanuel F. Petricoin, III, Dunkirk, MD (US)

(73) Assignees: Correlogic Systems, Inc., Rockville, MD (US); The United States of America as represented by the Department of Health and Human Services, Washington, DC (US)

( * ) Notice: Subject to any disclaimer, the term of this patent is extended or adjusted under 35 U.S.C. 154(b) by 368 days.

(21) Appl. No.: 10/628,137

(22) Filed: Jul. 28, 2003

(65) Prior Publication Data

US 2004/0058388 A1    Mar. 25, 2004

Related U.S. Application Data

(60) Provisional application No. 60/398,831, filed on Jul. 29, 2002.

(51) Int. Cl.
*G06F 19/00* (2006.01)
*G01N 24/00* (2006.01)

(52) U.S. Cl. ......................................... 702/19; 436/173
(58) Field of Classification Search ...................... None
See application file for complete search history.

(56) References Cited

U.S. PATENT DOCUMENTS

| | | | |
|---|---|---|---|
| 4,122,343 A | 10/1978 | Risby et al. | |
| 4,697,242 A | 9/1987 | Holland et al. | |
| 4,881,178 A | 11/1989 | Holland et al. | |
| 5,136,686 A | 8/1992 | Koza | |
| 5,352,613 A | 10/1994 | Tafas et al. | |
| 5,649,030 A | 7/1997 | Normile et al. | |
| 5,687,716 A | 11/1997 | Kaufmann et al. | |
| 5,697,369 A | 12/1997 | Long, Jr. et al. | |
| 5,716,825 A | 2/1998 | Hancock et al. | |
| 5,719,060 A | 2/1998 | Hutchens et al. | |
| 5,790,761 A | 8/1998 | Heseltine et al. | |
| 5,839,438 A | 11/1998 | Graettinger et al. | |
| 5,905,258 A | 5/1999 | Clemmer et al. | |
| 5,946,640 A | 8/1999 | Goodacre et al. | |
| 5,974,412 A | 10/1999 | Hazlehurst et al. | |
| 6,025,128 A | 2/2000 | Veltri et al. | |
| 6,081,797 A | 6/2000 | Hitt | |
| 6,128,608 A | 10/2000 | Barnhill | |
| 6,157,921 A | 12/2000 | Barnhill | |
| 6,225,047 B1 | 5/2001 | Hutchens et al. | |
| 6,295,514 B1 | 9/2001 | Agrafiotis et al. | |
| 6,329,652 B1 | 12/2001 | Windig et al. | |
| 6,427,141 B1 | 7/2002 | Barnhill | |
| 6,558,902 B1 | 5/2003 | Hillenkamp | |
| 6,571,227 B1 | 5/2003 | Agrafiotis et al. | |
| 6,579,719 B1 | 6/2003 | Hutchens et al. | |
| 6,615,199 B1 | 9/2003 | Bowman-Amuah | |
| 6,675,104 B2 | 1/2004 | Paulse et al. | |
| 6,680,203 B2 | 1/2004 | Dasseux et al. | |
| 6,844,165 B2 | 1/2005 | Hutchens et al. | |
| 6,925,389 B2 | 8/2005 | Hitt et al. | |
| 2002/0046198 A1 | 4/2002 | Hitt | |
| 2002/0138208 A1 | 9/2002 | Paulse et al. | |
| 2002/0193950 A1 | 12/2002 | Gavin et al. | |
| 2003/0054367 A1 | 3/2003 | Rich et al. | |
| 2003/0077616 A1 | 4/2003 | Lomas | |
| 2003/0129589 A1 | 7/2003 | Koster et al. | |
| 2003/0134304 A1 | 7/2003 | van der Greef et al. | |

FOREIGN PATENT DOCUMENTS

| WO | WO 93/05478 A1 | 3/1993 |
|---|---|---|
| WO | WO 99/41612 | 8/1999 |
| WO | WO 99/47925 A2 | 9/1999 |
| WO | WO 99/58972 A1 | 11/1999 |
| WO | WO 00/49410 A3 | 8/2000 |
| WO | WO 00/55628 A1 | 9/2000 |
| WO | WO 01/20043 A1 | 3/2001 |
| WO | WO 01/31579 A2 | 5/2001 |
| WO | WO 01/31580 A2 | 5/2001 |
| WO | WO 01/84140 A2 | 11/2001 |
| WO | WO 02/06829 A2 | 1/2002 |
| WO | WO 02/059822 A2 | 8/2002 |

(Continued)

OTHER PUBLICATIONS

Loging, TW et al., "Identifying Potential Tumor Markers and Antigens by Database Mining and Rapid Expression Screening," Genome Research, 10(9):1393-1402 (Sep. 2000).

(Continued)

*Primary Examiner*—Lori A. Clow
(74) *Attorney, Agent, or Firm*—Cooley Godward Kronish LLP (57) ABSTRACT

The present invention relates to a method of quality assurance/quality control for high-throughput bioassay processes. The method includes generating a bioassay process model, and then comparing spectral data based on a combination of a biochip and a test serum to the bioassay process model to determine if the test sample and the bioassay process are producing acceptable data. Alternatively, the method may include comparing spectral data based on a combination of serum and diluents used in an electrospray process to the bioassay process model. If the bioassay process and test sample fall within the model, then the spectrum produced may be further analyzed.

27 Claims, 6 Drawing Sheets

FOREIGN PATENT DOCUMENTS

| | | |
|---|---|---|
| WO | WO 02/088744 A2 | 11/2002 |
| WO | WO 03/031031 A1 | 4/2003 |

OTHER PUBLICATIONS

Krishnamurthy, T. et al. "Detection of Pathogenic and Non-Pathogenic Bacteria by Matrix-assisted Laser Desorption.Ionization Time-of-flight Mass Spectrometry," Rapid Comms. in Mass Spectrometry, vol. 10, 883-888 (1996).

Adam, B-L et al., "Serum Protein Fingerprinting Coupled with a Pattern-matching Algorithm Distinguishes Prostate Cancer from Benign Prostate Hyperplasia and Healthy Men," Cancer Research 62, 3609-3614 (Jul. 1, 2002).

Li, J. et al. "Proteomics and Bioinformatics Approaches for Identification of Serum Biomarkers to Detect Breast Cancer," Clinical Chemistry 48:8, 1296-1304 (2002).

Petricion III, E.F. et al., "Use of proteomic patterns in serum to identify ovarian cancer," The Lancet, vol. 359, 572-577 (Feb. 16, 2002).

Brown, M.P.S. et al. "Knowledge-based analysis of microarray gene expression data by using support vector machines," PNAS vol. 97, No. 1, pp. 262-267 (Jan. 4, 2000).

Kiem, H. & Phuc, D, "Using Rough Genetic and Kohonen's Neural Network for Conceptual Cluster Discovery in Data Mining," New Directions in Rough Sets, Data Mining and Granular-Soft Computing. International Workshop, RSFDGRC Proceedings, pp. 448-452 (Nov. 9, 1999).

Chang, E.I et al., "Using Genetic Algorithms to Select and Create Features for Pattern Classification," UCNN International Joint Conf. on Neural Networks, pp. 111-747 to 111-752 (Jan. 8, 1991).

Rosty C. et al., "Identification of Hepatocarcinoma-Intestine-Pancreas/Pancreatitis-associated Protein I as a Biomarker for Pancreatic Ductal Adenocarcinoma by Protein Biochip Technology," Cancer Research 62:1868-75 (Mar. 15, 2002).

Claydon, M.A., "The rapid identification of intact microorganisms using mass spectrometry," Nature Biotech. 14:1584-1586 (Nov. 1996).

Bittl, J.A., "From Confusion to Clarity: Direct Thrombin Inhibitors for Patients with Heparin-Induced Thrombocytopenia," Cath. and Cardio. Interventions 52:473-475 (2001).

Paweletz, C.P.. "Rapid Protein Display Profiling of Cancer Progression Directly from Human Tissue Using a Protein Biochip," Drug Development Research 49:34-42 (2000).

Ciphergen European Update, 1:1-4 (2001).

Kohonen, T. Self Organizing Maps (Springer 2001), pp. 1-70.

Jun Zhang, *Dynamics and Formation of Self-Organizing Maps*, in "Self-Organizing Map Formation: Foundations of Neural Computation," pp. 55-67 (Klaus Obermayer & Terrence J. Sejnowski eds.) (2001).

Kohonen, T. "Self-Organization and Associative Memory" (Springer 1988), pp. 30-67.

Holland, J.H., "Adaption in Natural and Artifical Systems: An Introductory Analysis with Applications to Biology, Control, and Artifical Intelligence" (MIT Press 2001), pp. 1-31; 89-120.

Alaiya, A.A. et al., "Classification of Human Ovarian Tumors Using Multivariate Data Analysis of Polypeptide Expression Patterns," Int. J. Cancer, 2000, pp. 731-736, vol. 86.

Ashfaq, R. et al., "Evaluation of PAPNET™ System for Rescreening of Negative Cervical Smears," Diagnostic Cytopathology, 1995, pp. 31-36, vol. 13, No. 1.

Astion, M. L. et al., "The Application of Backpropagation Neural Networks to Problems in Pathology and Laboratory Medicine," Arch Pathol Lab Med, Oct. 1992, pp. 995-1001, vol. 116.

Atkinson, E. N. et al., "Statistical Techniques for Diagnosing CIN Using Fluorescence Spectroscopy: SVD and CART," Journal of Cellular Biochemistry, 1995, Supplement 23, pp. 125-130.

Babaian, R. J. et al., "Performance of a Neural Network in Detecting Prostate Cancer in the Prostate-Specific Antigen Reflex Range of 2.5 to 4.0 ng/ml," Urology, 2000, pp. 1000-1006, vol. 56, No. 6.

Bailey-Kellogg, C. et al., "Reducing Mass Degeneracy in SAR by MS by Stable Isotopic Labeling," Journal of Computational Biology, 2001, pp. 19-36, vol. 8, No. 1.

Belic, I. et al., "Neural Network Methodologies for Mass Spectra Recognition," Vacuum, 1997, pp. 633-637, vol. 48, No. 7-9.

Belic, I., "Neural Networks Methodologies for Mass Spectra Recognition," pp. 375-380., additional details unknown, 1995.

Berikov, V. B. et al., "Regression Trees for Analysis of Mutational Spectra in Nucleotide Sequences," Bioinformatics, 1999, pp. 553-562, vol. 15, Nos. 7/8.

Breiman, L. et al., Classification and Regression Trees, Boca Raton, Chapman & Hall/CRC, 1984, pp. 174-265 (Ch. 6, Medical Diagnosis and Prognosis).

Cairns, A. Y. et al., "Towards the Automated Prescreening of Breast X-Rays," Alistair Cairns, Department of Mathematics & Computer Science, University of Dundee, pp. 1-5, 1992.

Caprioli, R. M. et al., "Molecular Imaging of Biological Samples: Localization of Peptides and Proteins Using MALDI-TOF MS," Analytical Chemistry, 1997, pp. 4751-4760, vol. 69, No. 23.

Chace, D. H. et al., "Laboratory Integration and Utilization of Tandem Mass Spectrometry in Neonatal Screening: A Model for Clinical Mass Spectrometry in the Next Millennium," Acta Paediatr. Suppl. 432, 1999, pp. 45-47.

Christiaens, B. et al., "Fully Automated Method for the Liquid Chromatographic-Tandem Mass Spectrometric Determination of Cyproterone Acetate in Human Plasma using Restricted Access Material for On-Line Sample Clean-Up", Journal of Chromatography A, 2004, pp. 105-110, vol. 1056.

Chun, J. et al., "Long-term Identification of Streptomycetes Using Pyrolysis Mass Spectrometry and Artificial Neural Networks," Zbl. Bakt., 1997, pp. 258-266, vol. 285, No. 2.

Cicchetti, D. V., "Neural Networks and Diagnosis in the Clinical Laboratory: State of the Art," Clinical Chemistry, 1992, pp. 9-10, vol. 38, No. 1.

Claydon, M. A., et al., "The Rapid Identification of Intact Microorganisms Using Mass Spectrometry," Abstract, 1 page, [online], [retrieved on Feb. 6, 2003]. Retrieved from the Internet <URL: http://www.ncbi.nlm.nih.gov/entrez/query.fcgi?cmd=Retrieve&dh=PubMed&list_uids+963 . . . >.

Crawford, L. R. et al., "Computer Methods in Analytical Mass Spectrometry; Empirical Identification of Molecular Class," Analytical Chemistry, Aug. 1968, pp. 1469-1474, vol. 40, No. 10.

Curry, B. et al., "MSnet: A Neural Network That Classifies Mass Spectra," Stanford University, Oct. 1990, To be published in Tetrahedron Computer Methodology, pp. 1-31.

De Brabandere, V. I. et al., Isotope Dilution-Liquid Chromatography/Electrospray Ionization-Tandem Mass Spectrometry for the Determination of Serum Thyroxine as a Potential Reference Method, Rapid Communications in Mass Spectrometry, 1998, pp. 1099-1103, vol. 12.

Dhar, V., et al., Seven Methods for Transforming Corporate Data Into Business Intelligence, Upper Saddle River, N.J., Prentice Hall, 1997, pp. 52-76.

Dudoit, S. et al., "Comparison of Discrimination Methods for the Classification of Tumors using Gene Expression Data," UC Berkeley, Mar. 7, 2000, pp. 1-51, [online], [retrieved on Apr. 4, 2002]. Retrieved from the internet <URL: http://stat-www.berkeley.edu/users/terry/zarray/Html/discr.html>.

Dudoit, S. et al., "Comparison of Discrimination Methods for the Classification of Tumors Using Gene Expression Data," Mathematical Sciences Research Institute, Berkeley, CA, Technical Report # 576, Jun. 2000, pp. 1-43.

Dzeroski, S. et al., "Diterpene Structure Elucidation from 13C NMR-Spectra with Machine Learning," Boston, Kluwer Academic Publishers, Intelligent Data Analysis in Medicine and Pharmacology, 1997, pp. 207-225.

Eghbaldar, A. et al., "Identification of Structural Features from Mass Spectrometry Using a Neural Network Approach: Application to Trimethylsilyl Derivatives Used for Medical Diagnosis," J. Chem. Inf. Comput. Sci., 1996, pp. 637-643, vol. 36, No. 4.

Freeman, R. et al., "Resolution of Batch Variations in Pyrolysis Mass Spectrometry of Bacteria by the Use of Artificial Neural Network Analysis," Antonie van Leeuwenhock, 1995, pp. 253-260, vol. 68.

Furlong, J. W. et al., "Neural Network Analysis of Serial Cardiac Enzyme Data; A Clinical Application of Artificial Machine Intelligence," American Journal of Clinical Pathology, Jul. 1991, pp. 134-141, vol. 96, No. 1.

Gaskell, S. J., "Electrospray: Principles and Practice," Journal of Mass Spectrometry, 1997, pp. 677-688, vol. 32.

George, S. E., "A Visualization and Design Tool (AVID) for Data Mining with the Self-Organizing Feature Map," International Journal on Artificial Intelligence Tools, 2000, pp. 369-375, vol. 9, No. 3.

Goodacre, R. et al. "Rapid Identification of Urinary Tract Infection Bacteria Using Hyperspectral Whole-Organism Fingerprinting and Artificial Neural Networks.," Microbiology, 1998, pp. 1157-1170, vol. 144.

Goodacre, R. et al., "Correction of Mass Spectral Drift Using Artificial Neural Networks," Analytical Chemistry, 1996, pp. 271-280, vol. 68.

Goodacre, R. et al., "Discrimination between Methicillin-Resistant and Methicillin-Susceptible *Staphylococcus aureus* Using Pyrolysis Mass Spectrometry and Artificial Neural Networks," Journal of Antimicrobial Chemotherapy, 1998, pp. 27-34, vol. 41.

Goodacre, R. et al., "Identification and Discrimination of Oral Asaccharolytic Eubacterium spp. by Pyrolysis Mass Spectrometry and Artificial Neural Networks," Current Microbiology, 1996, pp. 77-84, vol. 32.

Goodacre, R. et al., "Quantitative Analysis of Multivariate Data Using Artificial Neural Networks: A Tutorial Review and Applications to the Deconvolution of Pyrolysis Mass Spectra," Zbl. Bakt., 1996, pp. 516-539, vol. 284.

Goodacre, R. et al., "Sub-species Discrimination, Using Pyrolysis Mass Spectrometry and Self-organising Neural Networks, of Propionibacterium acnes Isolated from Normal Human Skin," Zbl. Bakt., 1996, pp. 501-515, vol. 284.

Gray, N. A. B., "Constraints on 'Learning Machine' Classification Methods," Analytical Chemistry, Dec. 1976, pp. 2265-2268, vol. 48, No. 14.

Hackett, P. S. et al., "Rapid SELDI Biomarker Protein Profiling of Serum from Normal and Prostate Cancer Patients," American Association for Cancer Research (abstract only), Mar. 2000, pp. 563-564, vol. 41.

Halket, J. M. et al., "Deconvolution Gas Chromatography/Mass Spectrometry of Urinary Organic Acids—Potential for Pattern Recognition and Automated Identification of Metabolic Disorders," Rapid Communication in Mass Spectrometry, 1999, pp. 279-284, vol. 13.

Hashemi, R. R. et al., "Identifying and Testing of Signatures for Non-Volatile Biomolecules Using Tandem Mass Spectra," SIGBIO Newsletter, Dec. 1995, pp. 11-19, vol. 15, No. 3.

Hausen, A. et al., "Determination of Neopterine in Human Urine by Reversed-Phase High-Performance Liquid Chromatography," Journal of Chromatography, 1982, pp. 61-70, vol. 227.

Hess, K. R. et al., "Classification and Regression Tree Analysis of 1000 Consecutive Patients with Unknown Primary Carcinoma," Clinical Cancer Research, Nov. 1999, pp. 3403-3410, vol. 5.

Jain, A. K. et al., "Statistical Pattern Recognition: A Review," IEEE Transcations on Pattern Analysis and Machine Intelligence, Jan. 2000, pp. 4-37, vol. 22, No. 1.

Jellum, E. et al., "Mass Spectrometry in Diagnosis of Metabolic Disorders," Biomedical and Environmental Mass Spectrometry, 1988, pp. 57-62, vol. 16.

Jurs, P. C. et al., "Computerized Learning Machines Applied to Chemical Problems; Molecular Formula Determination from Low Resolution Mass Spectrometry," Analytical Chemistry, Jan. 1969, pp. 21-27, vol. 41, No. 1.

Kenyon, R. G. W. et al., "Application of Neural Networks to the Analysis of Pyrolysis Mass Spectra," Zbl. Bakt., 1997, pp. 267-277, vol. 285.

Kohavi, R. et al., "Wrappers for Feature Subset Selection," Artificial Intelligence, 1997, pp. 273-324, vol. 97.

Kohno, H. et al., "Quantitative Analysis of Scintiscan Matrices by Computer," Japanese Journal of Medical Electronics and Biological Engineering, Aug. 1974, pp. 22-29.

Lewis, R. J., "An Introduction to Classification and Regression Tree (CART) Analysis," presented at 2000 Annual Meeting of the Society for Academic Emergency Medicine in San Franciso, California, 2000, pp. 1-14.

Liotta, L. et al., "Molecular Profiling of Human Cancer," Nature Genetics, Oct. 2000, pp. 48-56, vol. 1.

Lockhart, D. J. et al., "Genomics, Gene Expression and DNA Arrays," Nature, Jun. 2000, pp. 827-836, vol. 405.

Lowry, S. R. et al., "Comparison of Various K-Nearest Neighbor Voting Schemes with the Self-Training Interpretive and Retrieval System for Identifying Molecular Substructures from Mass Spectral Data," Analytical Chemistry, Oct. 1977, pp. 1720-1722, vol. 49, No. 12.

Luo, Y. et al., Quantification and Confirmation of Flunixin in Equine Plasma by Liquid Chromatograph—Quadrupole Time-Of-Flight Tandem Mass Spectrometry, Journal of Chromatography B, 2004, pp. 173-184, vol. 801.

Macfie, H. J. H. et al., "Use of Canonical Variates Analysis in Differentiation of Bacteria by Pyrolysis Gas-Liquid Chromatography," Journal of General Microbiology, 1978, pp. 67-74, vol. 104.

Malins, D. C. et al., "Models of DNA Structure Achieve Almost Perfect Discrimination Between Normal Prostate, Benign Prostatic Hyperplasia (BPH), and Adenocarcinoma and Have a High Potential for Predicting BPH and Prostrate Cancer," Proceedings of the National Academy of Sciences, Jan. 1997, pp. 259-264, vol. 94.

Marvin, L. F. et al., "Characterization of a Novel Sepia Officinalis Neuropeptide using MALDI-TOL MS and Post-Source Decay Analysis," Peptides, 2001, pp. 1391-1396, vol. 22.

Meuzelaar, H. L. C. et al., "A Technique for Fast and Reproducible Fingerprinting of Bacteria by Pyrolysis Mass Spectrometry," Analytical Chemistry, Mar. 1973, pp. 587-590, vol. 45, No. 3.

Meyer, B. et al., "Identification of the 1H-NMR Spectra of Complex Oligosaccharides with Artificial Neural Networks," Science, Feb. 1991, pp. 542-544, vol. 251.

Microsoft Press, Computer Dictionary, Second Edition, The Comprehensive Standard for Business, School, Library, and Home, Microsoft Press, Redmond, WA, 1994, pp. 87 and 408.

Moler, E. J. et al., "Analysis of Molecular Profile Data Using Generative and Discriminative Methods,", Physiol. Genomics, Dec. 2000, pp. 109-126, vol. 4.

Nikulin, A. E. et al., "Near-Optimal Region Selection for Feature Space Reduction: Novel Preprocessing Methods for Classifying MR Spectra," NMR Biomedicine, 1998, pp. 209-216, vol. 11.

Nilsson, T. et al., "Classification of Species in the Genus Penicillium by Curie Point Pyrolysis/Mass Spectrometry Followed by Multivariate Analysis and Artificial Neural Networks," Journal of Mass Spectrometry, 1996, pp. 1422-1428, vol. 31.

Oh, J. M. C. et al., "A Database of Protein Expression in Lung Cancer," Proteomics, 2001, pp. 1303-1319, vol. 1.

Pei, M. et al. "Feature Extraction Using Genetic Algorithms," Proceedings of the 1st International Symposium on Intelligent Data Engineering and Learning, IDEAL '98, Oct. 1998, pp. 371-384, Springer, Hong Kong.

Petricoin, E. F., III et al., "Serum Proteomic Patterns for Detection of Prostate Cancer," Journal of the National Cancer Institute, Oct. 16, 2002, pp. 1576-1578, vol. 94, No. 20.

Petricoin, E. F. et al., "Clinical Applications of Proteomics," Journal of Nutrition [online], Jul. 2003 [retrieved on Jan. 18, 2005], pp. 1-19, vol. 133, No. 7. Retrieved from the Internet: <URL: http://www.nutrition.org/cgi/content/full/133/7/2476S.

Prior, C. et al., "Potential of Urinary Neopterin Excretion in Differentiating Chronic Non-A, Non-B Hepatitis from Fatty Liver," The Lancet, Nov. 28, 1987, pp. 1235-1237.

Reed, J. "Trends in Commerical Bioinformatics," Oscar Gruss Biotechnology Review, Mar. 2000, pp. 1-20.

Reibnegger, G. et al., "Neural Networks as a Tool for Utilizing Laboratory Information: Comparison with Linear Discriminant Analysis and with Classification and Regression Trees," Proceedings of the National Academy of Sciences, Dec. 1991, pp. 11426-11430, vol. 88.

Ricketts, I. W. et al., "Towards the Automated Prescreening of Cervical Smears," Mar. 11, 1992, Applications of Image Processing in Mass Health Screening, IEE Colloquium, pp. 1-4.

Roses, A.D., "Pharmacogenetics and the Practice of Medice," Nature, Jun. 15, 2000, pp. 857-865, vol. 405.

Salford Systems, "Salford Systems White Paper Series," pp. 1-17 [online], [retrieved on Oct. 17, 2000]. Retrieved from the internet: <URL: http//www.salford-systems.com/whitepaper.html>.

Schroll, G. et al., "Applications of Artificial Intelligence for Chemical Inference, III. Aliphatic Ethers Diagnosed by Their Low-Resolution Mass Spectra and Nuclear Magnetic Resonance Data," Journal of the American Chemical Society, Dec. 17, 1969, pp. 7440-7445.

Shaw, R. A. et al., "Infrared Spectroscopy of Exfoliated Cervical Cell Specimens," Analytical and Quantitative Cytology and Histology, Aug. 1999, pp. 292-302, vol. 21, No. 4.

Shevchenko, A. et al., "MALDI Quadupole Time-of-Flight Mass Spectrometry: A Powerful Tool for Proteomic Research," Analytical Chemistry, May 1, 2000, pp. 2132-2141, vol. 72, No. 9.

Strouthopoulos, C. et al., "PLA Using RLSA and a Neural Network," Engineering Applications of Artificial Intelligence, 1999, pp. 119-138, vol. 12.

Taylor, J. et al., "The Deconvolution of Pyrolysis Mass Spectra Using Genetic Programming: Application to the Identification of Some Eubacterium Species," FEMS Microbiology Letters, 1998, pp. 237-246, vol. 160.

Tong, C. S. et al., "Mass Spectral Search method using the Neural Network approach," International Joint Conference on Neural Networks, Washington, DC Jul. 10-16, 1999, Proceedings, vol. 6 of 6, pp. 3962-3967.

Tong, C. S. et al., "Mass spectral search method using the neural network approach," Chemometrics and Intelligent Laboratory Systems, 1999, pp. 135-150, vol. 49.

Von Eggeling, F. et al, "Mass Spectrometry Meets Chip Technology: A New Proteomic Tool in Cancer Research?," Electrophoresis, 2001, pp. 2898-2902, vol. 22, No. 14.

Voorhees, K. J. et al., "Approaches to Pyrolysis/Mass Spectrometry Data Analysis of Biological Materials," in: Meuzelaar, H. L. C., Computer-Enhanced Analytical Spectroscopy, vol. 2, New York, Plenum Press, 1990, pp. 259-275.

Werther, W. et al., "Classification of Mass Spectra; a Comparison of Yes/No Classification Methods for the Recognition of Simple Structural Properties," Chemometrics and Intelligent Laboratory Systems, 1994, pp. 63-76, vol. 22.

Wythoff, B. J. et al., "Spectral Peak Verification and Recognition Using a Multilayered Neural Network," Analytical Chemistry, Dec. 15, 1990, pp. 2702-2709, vol. 62, No. 24.

Xiao, Z. et al., Quantitation of Serum Prostate-Specific Membrane Antigen by a Novel Protein Biochip Immunoassay Discriminates Benign from Malignant Prostate Disease, Cancer Research, Aug. 15, 2001, pp. 6029-6033, vol. 61.

Yao, X. et al., "Evolving Artificial Neural Networks for Medical Applications," Proceedings of the First Korea-Australia Joint Workshop on Evolutionary Computation, Sep. 1995, pp. 1-16.

Yates, J. R. III, "Mass Spectrometry and the Age of the Proteome," Journal of Mass Spectrometry, 1998, pp. 1-19, vol. 33.

Zhang, Z. "Combining Multiple Biomarkers in Clinical Diagnostics—A Review of Methods and Issues," Center for Biomarker Discovery, Department of Pathology, Johns Hopkins Medical Institutions, 14 pages, (2001).

Zhang, Z. et al., "Proteomics and Bioinformatics Approaches for Identification of Serum Biomarkers to Detect Breast Cancer," Clinical Chemistry, 2002, pp. 1296-1304, vol. 48, No. 8.

International Search Report for PCT Application No. PCT/US03/23505, filed Jul. 28, 2003, 3 pages.

FIG. 1

|   | CHIP | | | | |
|---|---|---|---|---|---|
|   | 1 | 2 | 3 | ••• | j |
| 1 | $MS_{1,1}$ | $MS_{2,1}$ | $MS_{3,1}$ | ••• | $MS_{j,1}$ |
| 2 | $MS_{1,2}$ | $MS_{2,2}$ | $MS_{3,2}$ | ••• | $MS_{j,2}$ |
| 3 | $MS_{1,3}$ | $MS_{2,3}$ | $MS_{3,3}$ | ••• | $MS_{j,3}$ |
| ⋮ | ⋮ | ⋮ | ⋮ | ⋮ | ⋮ |
| j | $MS_{1,i}$ | $MS_{2,i}$ | $MS_{3,i}$ | ••• | $MS_{j,i}$ |

SERUM SAMPLE

| Node | Count | State | StateSum | Error | m/z values | | | | | | | | |
|---|---|---|---|---|---|---|---|---|---|---|---|---|---|
| | | | | | 743.574 | 3872.046 | 2506.954 | 3012.083 | 2404.824 | 1146.171 | 1943.946 | 1531.685 | 5918.59 | 727.3972 |
| 0 | 26 | 1 | 26 | 0 | 0.0346 | 0.9975 | 0.3242 | 0.2673 | 0.3105 | 0.0184 | 0.1387 | 0.2726 | 0.5013 | 0.1472 |
| 1 | 89 | 0 | 2 | 2 | 0.0179 | 0.0829 | 0.0496 | 0.0369 | 0.0512 | 0.0097 | 0.0669 | 0.1422 | 1 | 0.0228 |
| 2 | 108 | 1 | 104 | 4 | 0.0242 | 1 | 0.0922 | 0.0684 | 0.0773 | 0.1016 | 0.0520 | 0.1295 | 0.1814 | 0.1078 |
| 3 | 23 | 0 | 0 | 0 | 0.0119 | 0.2537 | 0.0383 | 0.0352 | 0.0380 | 0.0149 | 0.3952 | 0.9198 | 0.8448 | 0.0457 |
| 4 | 6 | 0 | 0 | 0 | 0.0056 | 0.1851 | 0.0078 | 0.0123 | 0.0090 | 0.0269 | 0.9939 | 0.4465 | 0.5844 | 0.0117 |
| 5 | 1 | 1 | 1 | 1 | 0.0353 | 0.6777 | 0.1028 | 0.2074 | 0.0640 | 0 | 0.0936 | 0.4122 | 0.2605 | 1 |
| 6 | 2 | 1 | 2 | 0 | 0.3013 | 0.8013 | 0.5506 | 0.6894 | 0.8239 | 0.0709 | 0.2725 | 0.9569 | 0.8025 | 0.6541 |
| 7 | 1 | 0 | 0 | 0 | 0.1529 | 0 | 0 | 0 | 0 | 0.1529 | 0 | 0 | 0 | 1 |

Testing
Sensitivity 100%
Specificity 99%

Validation
Sensitivity 99%
Specificity 98%

QUALITY ASSURANCE/QUALITY CONTROL FOR HIGH THROUGHPUT BIOASSAY PROCESS

CROSS-REFERENCE TO RELATED APPLICATIONS

This application claims priority under 35 U.S.C. § 119(e) to U.S. Provisional Patent Application No. 60/398,831, entitled "Quality Assurance/Quality Control for SELDI-TOF Mass Spectra," filed on Jul. 29, 2002, the contents of which are hereby incorporated by reference in their entirety.

STATEMENT OF FEDERALLY SPONSORED RESEARCH

The research work described here was supported under a Cooperative Research and Development Agreement (CRADA) between the US Government and Correlogic Systems, Inc.

BACKGROUND OF THE INVENTION

The present invention relates generally to the field of bioinformatics. More specifically, the present invention relates to a method of quality assurance/quality control ("QA/QC") for bioinformatic systems.

Methods of analyzing biological samples are generally known. In a typical analysis, mass spectroscopy is performed on the biological sample to determine its overall biochemical make-up. Based on the mass spectra obtained from the mass spectroscopy, various diagnostics may be run.

When biological samples are analyzed, it is desirable to run more than one trial on the biological sample, thereby improving the accuracy of the diagnostic. Analysis of biological samples may be performed by using various high-throughput mass spectrometry related bioassay processes. A process can include using matrix assisted laser desorption ionization time-of-flight (MALDI-TOF) or electrospray techniques (i.e., generation of droplets by applying a high voltage to a stream of liquid). When performing multiple mass spectral analyses on the same sample, however, the spectra obtained can vary. This variation may be due to the mass spectrometer itself, from inconsistencies in the sample, heterogeneity in the patient population, or in sample handling and processing. A process that employed a protein chip or surface enhanced type of mass spectrometry (SELDI-TOF) indicated that various chips yielded spectra that were inconsistent with one another. Similar effects were observed with respect to spectra obtained using electrospray techniques. This inconsistency can lead to inaccurate results when running a diagnostic.

SUMMARY OF THE INVENTION

The present invention provides a QA/QC method for filtering out inconsistencies across high-throughput bioassay processes, particularly across different biochips and different diluents or concentrations of diluents used in electrospray techniques.

The present invention uses the Knowledge Discovery Engine ("KDE") to identify hidden patterns across a wide variety of serum samples and biochips to generate a control model and agnostic to the underlying disease processes in question. Electrospray, MALDI-TOF (Matrix Assisted Laser Desorption/Ionization-Time of Flight) mass spectra, or SELDI-TOF (Surface Enhanced Laser Desorption/Ionization-Time of Flight) mass spectra can be analyzed in this manner, for example. Alternatively, the invention may use the KDE to identify hidden patterns across a variety of serum to diluent concentrations to generate a control model. In yet another embodiment, the KDE may be used to identify hidden patterns across a variety of diluents and sera samples to generate a control model.

The KDE is disclosed in U.S. patent application Ser. No. 09/883,196, now U.S. Pat. No. 7,096,206, entitled "Heuristic Methods of Classification," filed Jun. 19, 2001 ("Heuristic Methods"), and U.S. patent application Ser. No. 09/906,661, now U.S. Pat. No. 6,925,389, entitled "A Process for Discriminating Between Biological States Based on Hidden Patterns from Biological Data," filed Jul. 18, 2001 ("Hidden Patterns"); the contents of both applications are hereby incorporated by reference in their entirety. Software running the KDE is available from Correlogic Systems, Inc., under the name Proteome Quest™.

After the KDE is used to generate a control model, a test serum may be compared to the control model to determine if the spectra produced by the high-throughput bioassay process and the serum are acceptable.

The KDE will search for hidden or subtle patterns of molecular expression that are, in and of themselves, "diagnostic." The level of the identified molecular products is termed per se diagnostic, because the level of the product is diagnostic without any further consideration of the level of any other molecular products in the sample.

In the data cluster analysis utilizing the KDE, the diagnostic significance of the level of any particular marker, e.g., a protein or transcript, is a function of the levels of the other elements that are used to calculate a sample vector. Such products are referred to as "contextual diagnostic products." The KDE's learning algorithm discovers wholly new classification patterns without knowing any prior information about the identity or relationships of the data pattern, i.e., without prior input that a specified diagnostic molecular product is indicative of a particular classification.

If the spectrum produced by the biochip and the serum map to the control model, then the data obtained from mass spectrometry of the serum and biochip may be used for further analysis. If the spectrum produced by the biochip and the serum fail to map to the control model, the data is deemed uncertified, and new data must be acquired. Alternatively, if a spectrum produced by a serum sample and a diluent map to the control model, then the spectrum obtained from an electrospray process may be used for further analysis. By using this method, inconsistencies across bioassay processes may be avoided, thereby improving the reliability of data obtained using the bioassay process. Other advantages may also be realized from the methods disclosed herein, as would be obvious to the ordinarily skilled artisan.

DETAILED DESCRIPTION

Generally, the invention includes a method of obtaining a control model for use in a bioinformatics system and a method for comparing a test sample against the model for the purpose of QA/QC.

Figure 1:
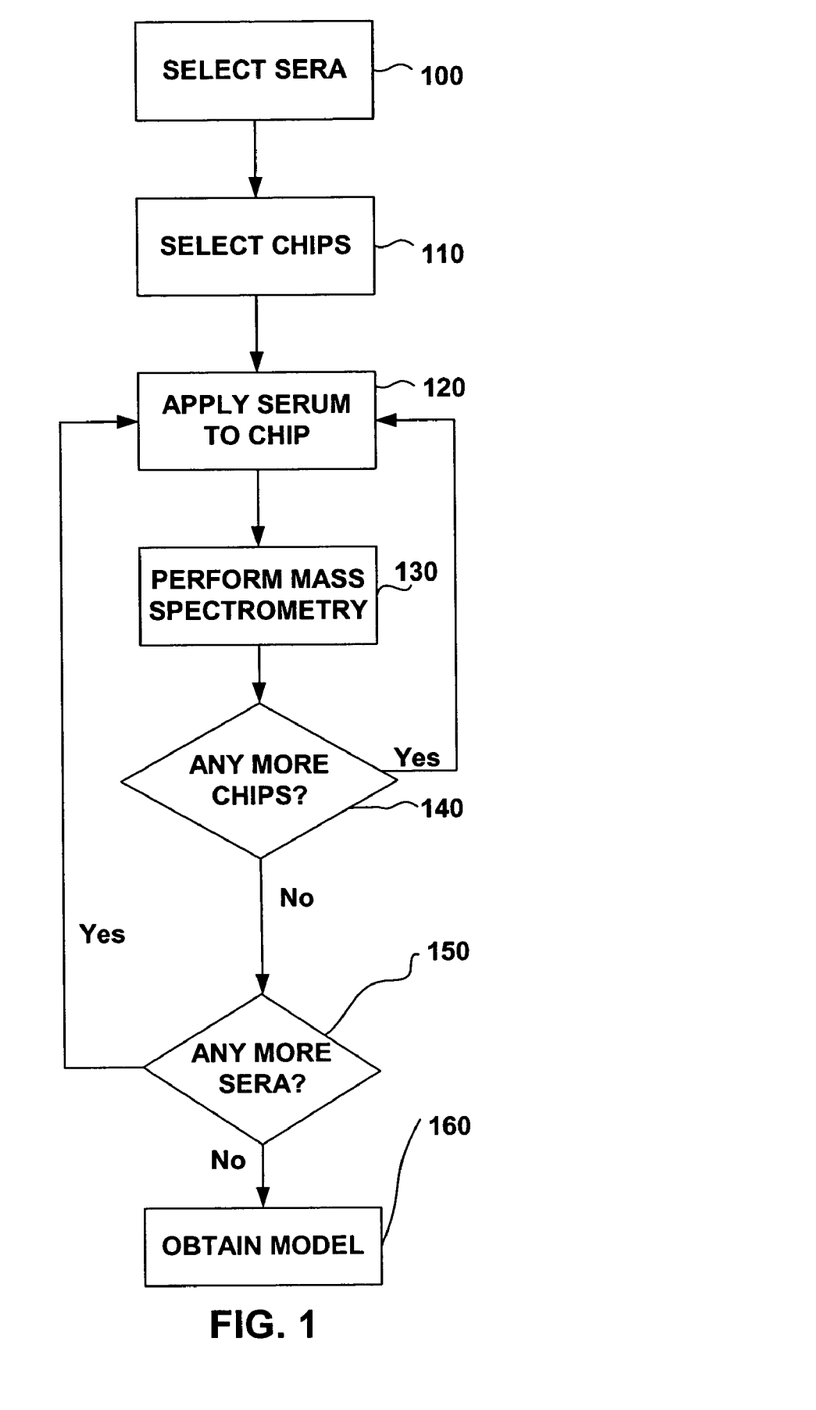
FIG. 1 is a flow chart illustrating a method of obtaining a control model.

A method of obtaining a control model according to one aspect of the present invention is illustrated in FIG. 1. To ensure a highly articulate model, a variety of serum samples are selected at step 100. The selection should include selecting serum from as diverse a group of individuals as possible. The more diverse the selected sera, the more articulate the control model will be. For example, sera may be taken from healthy males, healthy females, males afflicted with various diseases, females afflicted with various diseases, persons of different ages, and persons of different races.

Once the diverse group of sera has been selected, a group of different biochips is selected at step 110. The diverse group of biochips may include an anionic chip, a cationic chip, and an immobilized metal chip. The selection of chips may include at least one anionic chip and at least one cationic chip. However, in order to generate a workable model at least two chips should be selected. For example, one model could be generated using three types of chips: WCX2 (cationic exchange), SAX2 (anionic exchange), and IMAC3 (immobilized metal) surface enhanced laser desorption/ionization ("SELDI") chips.

After the initial selection of sera (100) and the selection of biochips (110), the sera are applied to the chips in step 120. After each serum is applied to the surface of a chip, then each chip and sera combination is analyzed by mass spectrometry at step 130 to obtain a spectral output characterized by mass to charge (m/z) values. After one spectrum is produced, the process is repeated for a different biochip/serum combination. Each time a spectrum is obtained for a particular biochip/serum combination, a determination is made at step 140 of whether all chips have been analyzed.

After all of the chips have been analyzed, a determination is made at step 150 of whether all sera have been analyzed by mass spectrometry in combination with each chip type. For example, assume three sera are selected at step 100, and two biochips are selected (one cationic exchange biochip ("Biochip A") and one anionic exchange biochip ("Biochip B")). After the first serum is analyzed by mass spectrometry on Biochip A, a determination is made at step 140 of whether all biochips have been used. Finding that the first serum has not been used with Biochip B, the process is repeated starting with step 120.

When both Biochip A and Biochip B have been analyzed with the first serum, a determination is made at step 150 of whether there are any more sera remaining. If any more sera remain, the process is repeated for each of the biochips. In this example, the process will be repeated for each of Biochip A and Biochip B, with the second and third sera respectively.

Figure 2:
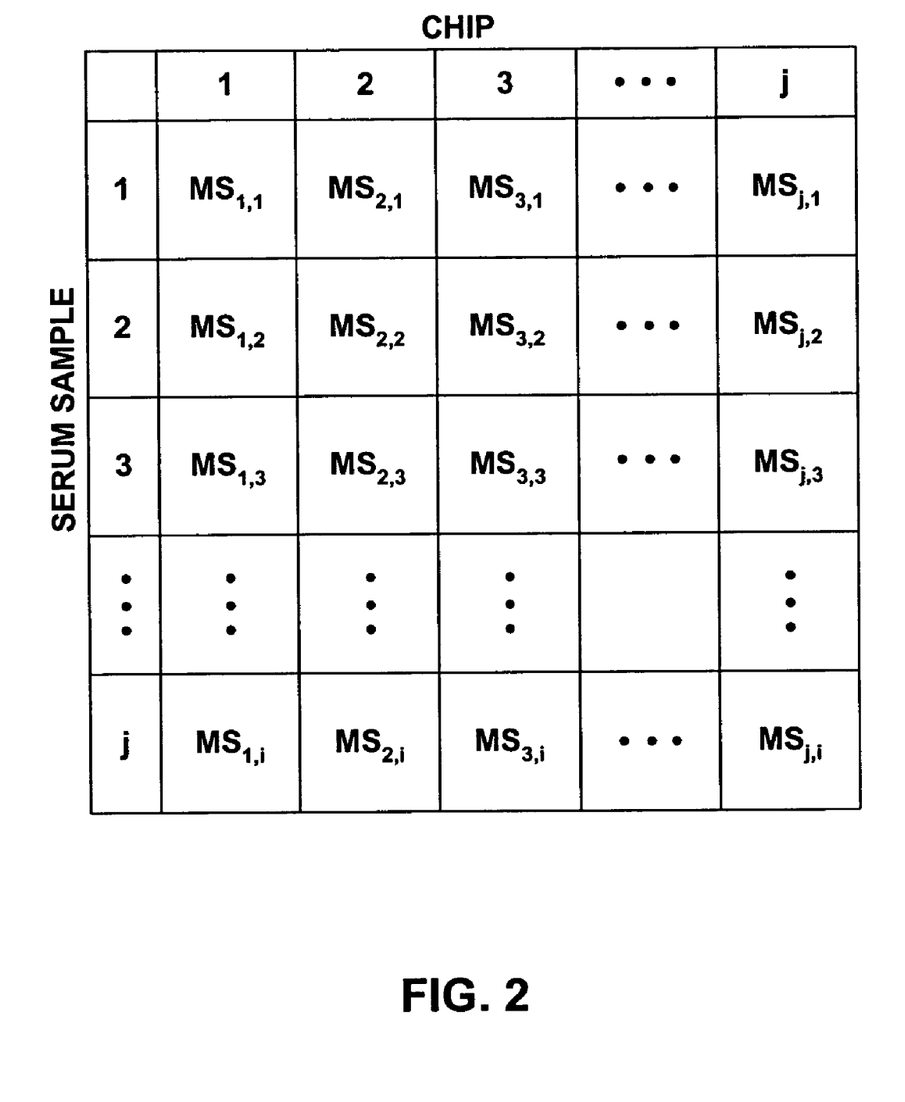
FIG. 2 depicts a table having various serum/biochip combinations that may be used to obtain the control model.

The data for each of the spectra may be stored, such as in the table illustrated in FIG. 2. The table includes data for "i" sera and "j" chips. Each cell in the table contains mass spectra (MS) data associated with each chip type and the various types of serum. For example, cell $MS_{j,i}$ corresponds to the spectral data from chip "j" and serum sample "i". After all of the data have been obtained, the stored mass spectrum data can be input into the KDE to discover hidden patterns in the spectral data.

Next, the process of developing a biochip model using the KDE will be described.

The data from each of the mass spectra are input into the KDE. The KDE then seeks to identify clusters of data (hidden patterns) in n-dimensional space, where n is the number of mass to charge values selected from the spectra for analysis, and each spectrum can be mapped into the n-dimensional space using the magnitude of each of the selected mass to charge values in the spectrum (the combination of a mass to charge value and the magnitude of the spectrum at that value being a vector). The KDE seeks clusters that contain as many of the spectra as possible and that distinguish each of the biochips from the others. Each cluster of data will define a centroid that will be associated with a particular biochip. In the event that a number of possible groupings or combinations of clusters are identified by the KDE, the user will select the most optimal grouping to define the biochip model. The selection process could be automated rather than being directly performed by the user. In either case, the cluster with the highest population of vectors can be identified by either the user or the system and that cluster can be designated as the control model.

Figure 3:
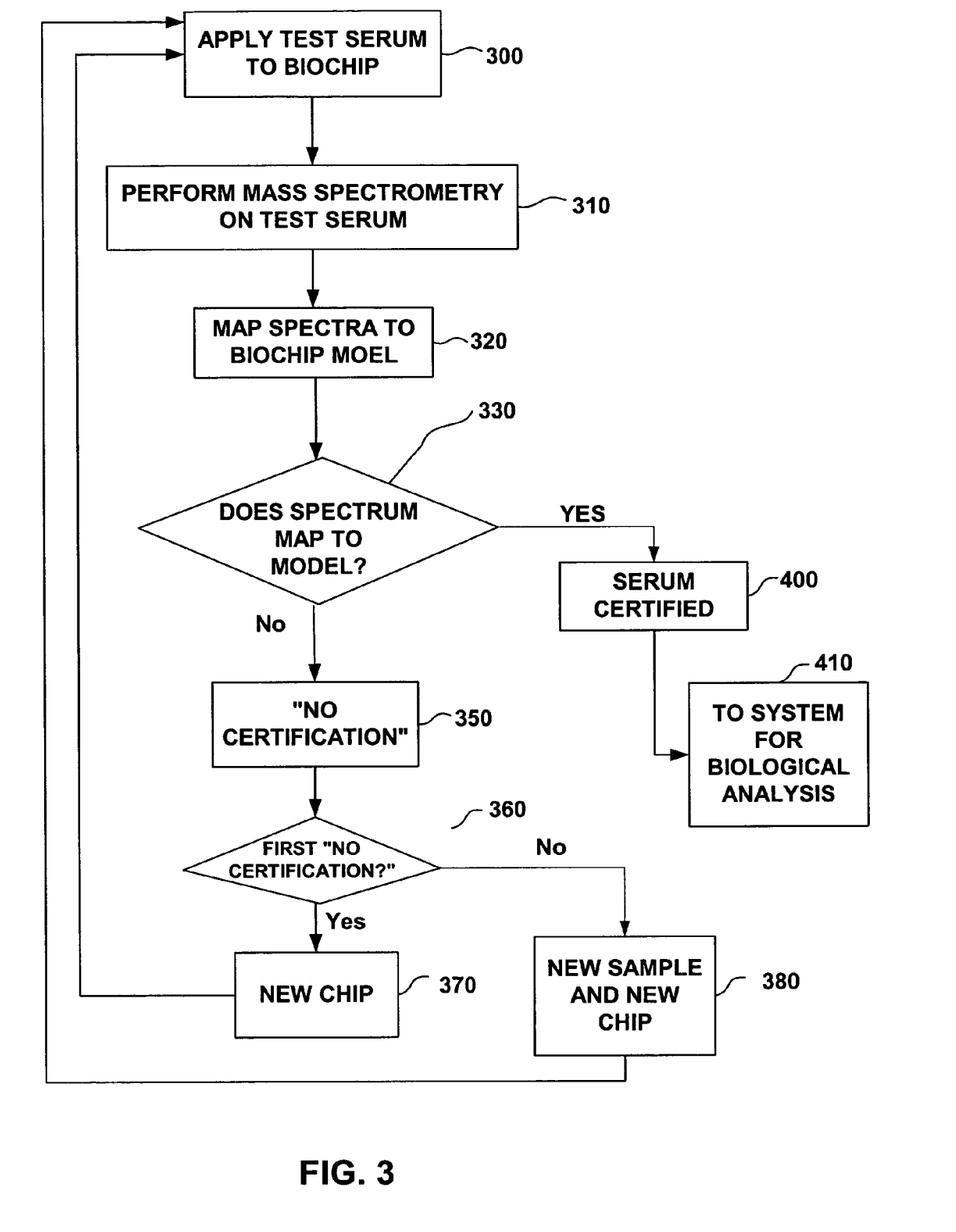
FIG. 3 illustrates a method of comparing the test serum to the control model.

After the model has been obtained, test sera may be run against the model to determine if the sera/biochip combination is certified for further analysis. One method of QA/QC using the biochip model obtained in FIG. 1 is depicted in FIG. 3.

First, in step 300 multiple samples from a test serum is applied to a biochip. The test serum could be serum intended for a cancer screening, for example. Then in step 310 the test serum samples are analyzed by mass spectrometry. The spectra obtained in step 310 are then mapped to the biochip model in step 320.

Mapping the spectrum to the biochip model is performed in manner similar to the mapping of a serum sample to a training data set to diagnose a particular disease state as described in the Hidden Patterns application. Mapping a spectrum to the biochip model includes determining the spectrum value for each of the n mass to charge ratios in the biochip mode, plotting the associated vectors in the model's n-dimensional space, and comparing them with the location of the model's centroid. The centroid is defined as the center of the cluster determined to have the highest population of vectors from the model development.

After the spectrum of the test sample is mapped to the biochip model, it is determined in a step 330 if the spectrum maps within a predetermined hypervolume centered on the centroid in the model associated with the tested biochip.

If the spectrum maps within the predetermined hypervolume, the spectrum is deemed certified for further analysis. If the map of the spectrum falls outside the predetermined hypervolume, the spectrum is not deemed certified and the sample must be reanalyzed.

A system employing the method of the present invention should operate within predetermined tolerances. In determining whether a spectrum for a sample maps to the model for the biochip used with the sample, the point to which the vectors from each sample spectrum maps in the model's n-dimensional space maps are compared to the location of the centroid for the cluster associated with the selected biochip. The spectrum is considered to map to the model if it lies within a predetermined hypervolume centered on that centroid. In this embodiment, the hypervolume defined with the centroid as its center will exclude approximately 95% of the total hypervolume of the n-dimensional space. The content of a polytope or other n-dimensional object is its generalized volume (i.e., its "hypervolume"). Just as a three-dimensional object has volume, surface area and generalized diameter, an n-dimensional object has "measures" of order 1, 2, ..., n, the hypervolume is defined based on these measures of order. The hypervolume can also be defined in terms of a predefined acceptable process tolerance. The n-dimensional hypervolume calculation is akin to Mahalanobis distances used in establishing rejection and acceptance criteria.

Figure 4:
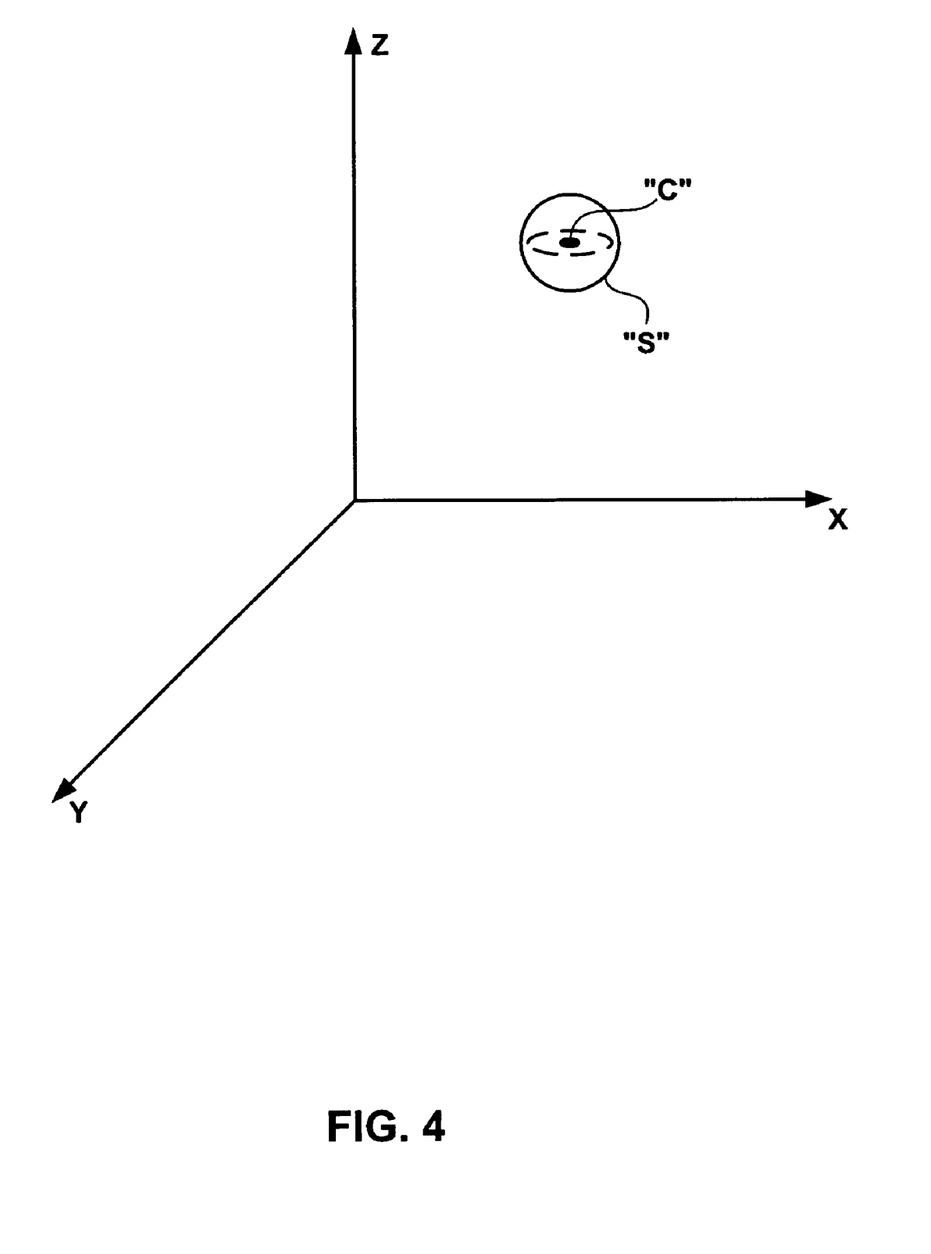
FIG. 4 is a depiction of mapping of exemplary tolerances in three-dimensional space according to one aspect of the present invention.

This can be visualized in three dimensions as depicted in FIG. 4. FIG. 4 illustrates a centroid "C," which is associated with the cluster of features plotted in n-dimensional space (here the space is depicted as three-dimensional for visualization purposes). A theoretical sphere, "S" is located in the n-dimensional space. The sphere is centered at the location of the centroid "C." Tolerances should be set such that the sphere "S" has a volume that excludes approximately 95% of the volume of the three-dimensional space. The volume of the three dimensional space is defined by the set of plotted features in that space, and is bounded by (and preferably normalized to) the m/z feature with the greatest intensity.

Referring back to FIG. 3, once a sample is deemed certified, the spectral data may be used for further analysis. The further analysis may entail running the data through the KDE to discover hidden patterns in the spectra. These hidden patterns may be compared to disease state models to diagnose for a particular disease. This method of diagnosis is described in further detail in the Hidden Patterns application.

If no spectra map to the model, then in step 350 the sample and biochip are deemed non-certified. If the sample and the chip were deemed non-certified the for the first time using a particular serum sample, then in steps 360 and 370 a determination is made to see if the "no certification" is a first "no certification"; is so, a new chip is selected and the process repeated.

If the sample and the biochip were determined to be non-certified more than once, then in step 380 a new serum sample and chip are obtained, and the process is repeated. After a certified sample has been obtained, at step 410 it is output for further analysis.

In one exemplary test, sera was obtained from subjects with and without cancer. Two types of biochips were selected, IMAC3 (immobilized metal) and WCX2 (cationic exchange). A diverse group of 256 sera were selected. The sera were then applied to each type of chip, analyzed by mass spectrometry, and the spectral output collected. The spectral data was input into the KDE.

Figure 5:
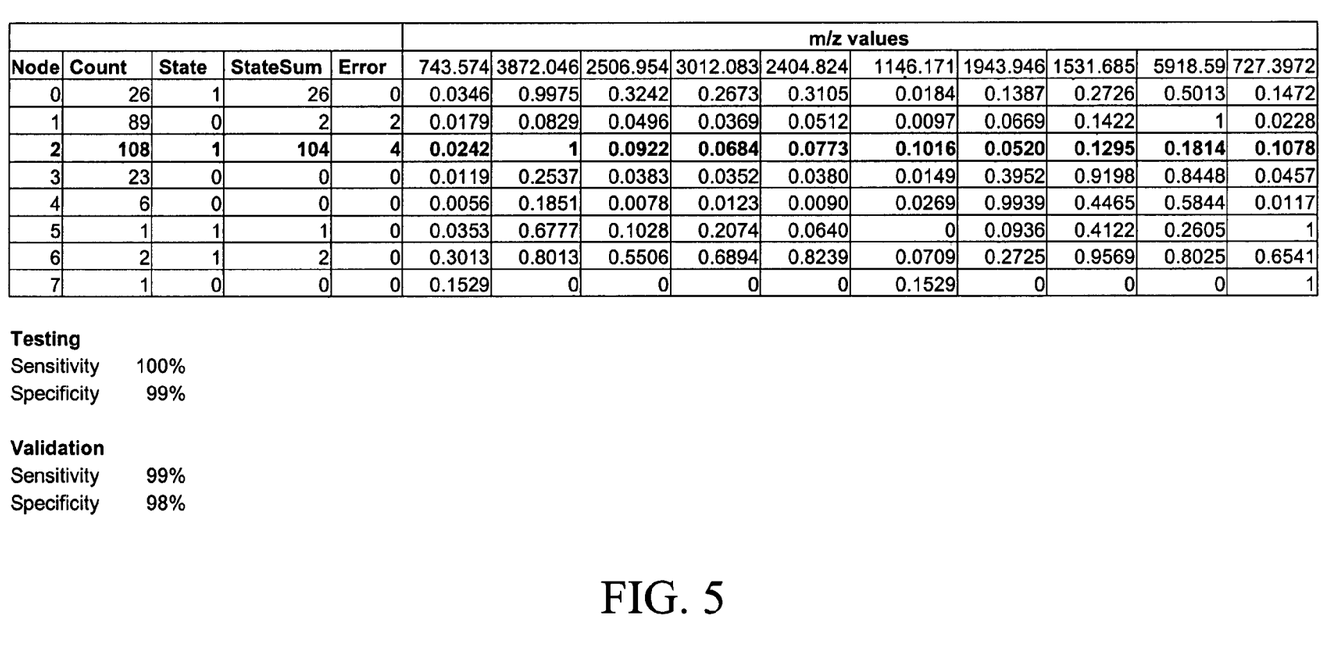
FIG. 5 is a table illustrating results obtained from the KDE using two different types of biochips and 256 sera.

The model identified by the KDE is shown in FIG. 5. The table in FIG. 5 shows the constituent "patterns" or clusters comprising the model. Each cluster corresponds to a point, or node, in the N-dimensional space defined by the N m/z values (or "features") included in the model. In this case, 10 m/z values are included in the model, so n=10. The table shows the constituent centroids of the mode, each in a row identified by a "Node" number. Thus, this model has eight nodes or centroids. The table also includes columns for the constituent features or vectors of the centroids, with the m/z value for each vector identified at the top of the column. The amplitudes are shown for each feature or m/z value, for each centroid, and are normalized to 1.0.

The remaining four columns in the table are labeled "Count," "State," "StateSum," and "Error." "Count" is the number of samples in the Training set that correspond to the identified node. "State" indicates the state of the node, where 1 indicates the IMAC3 chip and 0 indicates the WCX2 chip. "StateSum" is the sum of the state values for all of the correctly classified members of the indicated node, while "Error" is the number of incorrectly classified members of the indicated node. Thus, for node 2, 108 samples were assigned to the node, whereas 104 samples were actually from the IMAC3 chip. StateSum is thus 104 (rather than 108) and Error is 4.

The cluster that contained the highest population of vectors was designated as the control model. In the Example illustrated in FIG. 5, node 2 defined the control model because it contained the greatest number of vectors (108).

While the method described above has been described for use with biochips, another embodiment of the invention may be practiced using electrospray techniques to obtain data relating to a particular serum.

When using an electrospray technique for obtaining biological data for diagnostic purposes, a primary factor limiting the consistency of the data obtained is the particular diluents used in preparing the sample for electrospray analysis. Therefore, rather than characterizing the serum in conjunction with the biochips being used, electrospray techniques used in combination with the present methods will characterize the serum in combination with the diluents used.

To use electrospray ionization ("ESI") to obtain accurate spectral data, a stable spray should be obtained. There are three physical characteristics of the spectral data that yield spectral results that can be utilized by the KDE. These physical characteristics include: (1) the number of mass peaks; (2) the total ion current; and (3) the stability of the spray.

Various tests were run to determine a preferred diluent concentration and composition to yield effective results for use in the KDE. These tests were run using electrospray apparatus manufactured by Advion BioSciences, and particularly the NanoMate100™ ESI in conjunction with Correlogic's Proteome Pattern Blood Test™ which is based on the Proteome Quest™ software.

One particular test involved diluting the serum sample at 1:1000 in 50:50 acetonitrile: $H_2O$ containing 0.2% formic acid (FA). While 20 λ of each sample was aliquoted into each well, representing 0.02 λ of serum, only about 100-200 nano-liters was actually sprayed and analyzed. Operating the Q Star mass spectrometer in positive ion TOF/MS mode, data was acquired for 2 minutes/sample, m/z of 300-2000, using a 1 second scan rate. The nanospray was initiated by applying 1.55 kV spray voltage at a pressure of about 0.5 psi.

Based on testing of serum samples a determination was made that the Multichannel acquisition mode (MCA) should be used on the Q-star mass spectrometer when obtaining spectral data. This is based on a determination that the MCA mode produced better resolution of the spectral peaks.

To optimize the diluent used in preparing the serum samples, various other tests were run. The concentrations of the serum to diluent are preferably between 1:1000 and 1:250, but other diluent concentrations may be selected in a manner apparent to those skilled in the art. Two diluent types tested included acetonitrile (ACN) and methanol (MeOH). Each of these diluents was combined with an acid. Acids include, but are not limited to, trifluoroacetic acid (TFA), formic acid (FA), and acetic acid. Either TFA or FA can be used for purposes of the present invention and are preferably in concentrations between about 0.2% acid and 1.0% acid.

Figure 6:
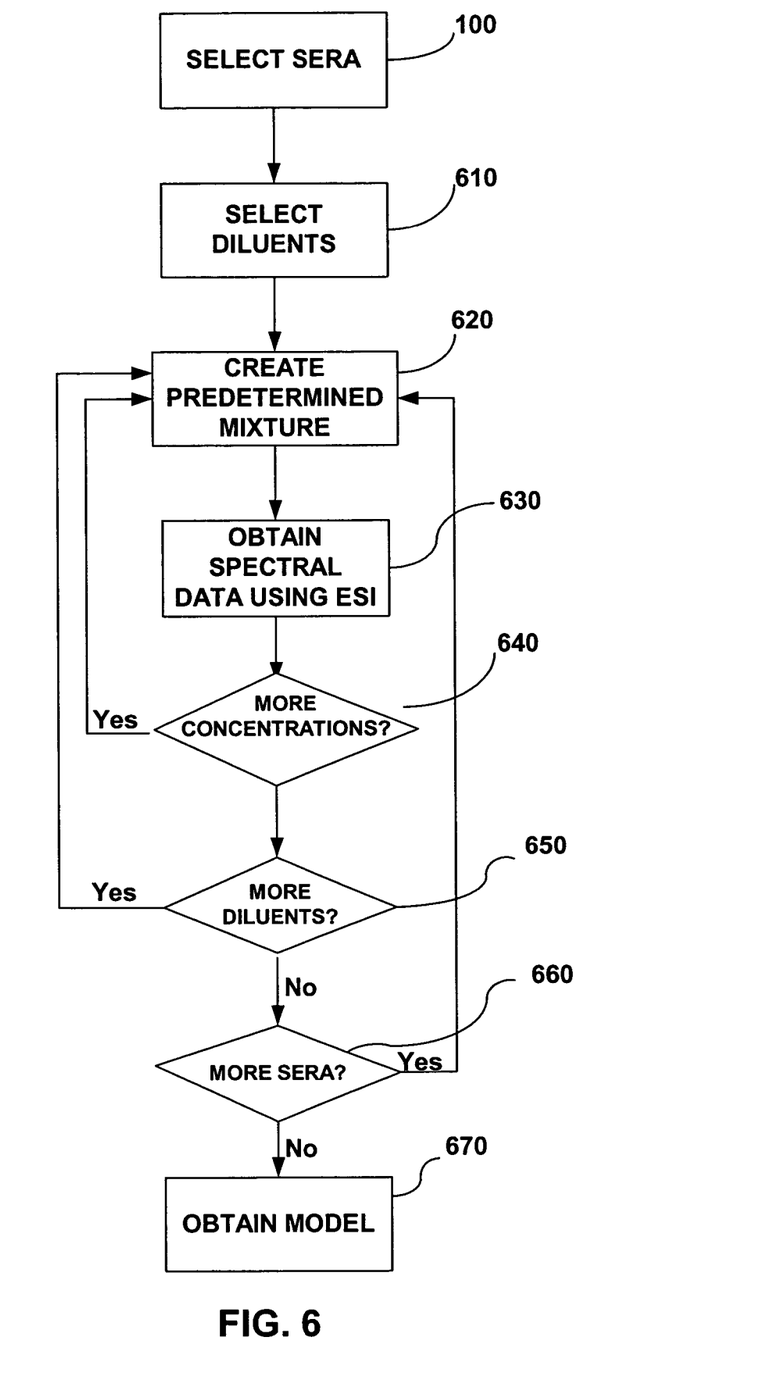
FIG. 6 is a flow chart of an alternative embodiment of the present invention for use with an electrospray process.

An alternative embodiment of the method of obtaining a model according to the present invention will now be described in relation to FIG. 6. The step of selecting sera in step 100 is the same as described above. Again, the more diverse the overall group of selected sera is, the more articulate the model will be.

Secondly, in step 610 a selection of diluents is made. Diluents selected may be diverse or homogeneous. For example, a diverse group of diluents including ACN and MeOH may be selected. Alternatively, only ACN may be selected as long as the concentrations of the ACN differ (e.g., 1:1000, 1:500, and 1:250 serum to ACN).

Thirdly, in step 620, a mixture is made according to predetermined concentrations of serum to diluent. This mixture is then analyzed using electrospray in step 630 to obtain spectral data. This process is repeated for all desired concentrations, diluents and serum samples until all data have been obtained in steps 640, 650, and 660. A model is then obtained in step 670 based on the data extracted from the various samples. The model is obtained using the KDE in the same manner as described above for the acquisition of a biochip model.

A method of QA/QC using the electrospray is substantially the same as for the disclosed method of QA/QC for biochips. Notable variations can be found in the generation of the sample and the method of obtaining the data. The significant differences between the overall processes stems from the differences in obtaining the model and its ability to identify a particular serum diluent.

In one particular test, sera were obtained from male and female subjects. Two diluents, acetonitrile (ACN) and methanol (MeOH) were selected. A mixture was made at a concentration of 1:250 of serum to diluent. Selected sera mixture (102 samples) were analyzed by electrospray mass spectrometry, and the spectral output collected. The spectral data was input into the KDE. The KDE identified a model containing three clusters in total that distinguished the two diluents. One cluster was associated with ACN and that cluster was designated as the control model.

The above-described method is applicable to various bioassay processes to ensure that both the particular high-throughput bioassay process being used and the serum being tested will yield an accurate diagnostic. By using the method described above, biological diagnostics may be provided that have increased accuracy and reliability.

Tolerances to employ the aforementioned methods were described as being such that a hypervolume defined about the centroid of a cluster that will exclude approximately 95% of the total hypervolume of the n-dimensional space. While 95% percent was explicitly mentioned, one of ordinary skill in the art would realize that the methods of the present invention would operate effectively with different sized hypervolumes centered on the centroid.

In the described embodiments, biochips and electrospray processes were illustrative. Various other high-throughput bioassay processes are known in the art and could be employed with the methods of the present invention.

In the described embodiments, to obtain a model characteristic of a particular high-throughput bioassay process, sera should be taken from healthy males, healthy females, males afflicted with a disease, females afflicted with a disease, persons of different ages and persons of different races. While these specific examples were given, numerous other diverse sera samples could be taken. The best possible diverse sera would contain serum from every individual in the world. Therefore, taking sera from any individual that does not group into one of the aforementioned classifications is within the scope of the present invention.

While specific diluents and acids were described in reference to the methods of QA/QC for electrospray techniques, these diluents and acids are not intended to be exhaustive and a variety of other suitable diluents and acids are suitable for those explicitly mentioned. Additionally, while specific concentrations of both acids and ratios of sera to diluent were disclosed, one of ordinary skill in the art will realize the specific concentrations will depend on the particular acids and diluents used to perform the inventive method, and the described acids and diluents are not intended to be all inclusive. Various other concentrations in combination with various acids and diluents will be obvious to the ordinarily skilled artisan based on the teachings of the present invention.

The various features of the invention have been described in relation to a method of quality assurance/quality control of high-throughput bioassay processes. However, it will be appreciated that many of the steps may be implemented with various apparatus and bioinformatics methods. Moreover, variations and modifications exist that would not depart from the scope of the invention.

We claim:

1. A method of determining whether mass spectral data from a test serum is acceptable for analysis in a bioassay using biochips, comprising:
    selecting a diverse group of sera, the diverse group of sera having different characteristics;
    obtaining information associated with a mass spectrum of each of the sera from the diverse group of sera using each of a plurality of control biochips;
    generating a control model based at least in part on the spectra obtained from the diverse group of sera, the control model including at least one centroid located in an n-dimensional space defined by n mass spectral features included in the control model;
    performing mass spectrometry on a test serum applied to a test biochip to obtain a test spectrum associated with the test serum;
    mapping the test spectrum to the n-dimensional space; and
    certifying that the test spectrum is acceptable for analysis in the bioassay if it is determined that the test spectrum maps to the n-dimensional space within an acceptable distance from said at least one centroid in the control model.

2. The method of claim 1, further comprising:
    classifying a biological state from the test spectrum based on a predetermined biological state model.

3. The method of claim 1, wherein if the test spectrum does not map to the n-dimensional space within an acceptable distance from said at least one centroid in the control model, and the test biochip is a first biochip, the method further comprising:
    repeating the steps of performing and mapping for a second biochip different from said test biochip.

4. The method of claim 1, said selecting further comprising:
    selecting at least two different sera from a pool of diverse sera, the pool of diverse sera consisting of: sera from healthy males, sera from healthy females, sera from males afflicted with a disease, sera from females afflicted with a disease, sera from persons of different races, and sera from people of different ages.

5. The method of claim 1, wherein said generating includes:
    identifying at least one cluster in common to the sera of the diverse group of sera and the plurality of different control biochips that contains said at least one centroid in the control model; and certifying that the test spectrum is acceptable for analysis in the bioassay if it is determined that the test spectrum maps to the n-dimensional space within said at least one cluster.

6. The method of claim 1, wherein the obtaining information includes:
obtaining information on sera applied to at least two types of biochips, the types of biochips being at least two of a cationic exchange biochip, an anionic exchange biochip, and an immobilized metal biochip.

7. The method of claim 1, wherein the test biochip is one of the plurality of different biochips.

8. The method of claim 1, wherein the test biochip is not one of the plurality of different biochips.

9. A method of determining whether mass spectral data from a test serum is acceptable for analysis in a bioassay employing a control model generated based on mass spectra obtained from application of a plurality of different sera to a plurality of different biochips, the control model including at least one centroid located in an n-dimensional space defined by n mass spectral features included in the model, comprising:
applying a test serum to a spot on a test biochip;
performing mass spectrometry on the test serum to obtain test spectral data associated with the test serum and the test biochip; and
mapping the test spectrum to the n-dimensional space; and
certifying that the test spectrum is acceptable for analysis in the bioassay if it is determined that the test spectrum maps to the n-dimensional space within an acceptable distance from said at least one centroid in the control model.

10. The method of claim 9, further comprising:
classifying a biological state from the test spectrum based on a predetermined biological state model.

11. The method of claim 9, wherein said performing mass spectrometry includes performing surface enhanced laser desorption/ionization time of flight (SELDI-TOF) mass spectrometry.

12. The method of claim 9, wherein said bioassay is capable of determining if the test serum exhibits a disease state.

13. A method of determining whether mass spectral data from a test serum is acceptable for analysis in a bioassay using a biochip, comprising:
providing in an n-dimensional space defined by n mass spectral features a location of at least one centroid associated with one biochip and that distinguishes the one biochip from at least one second biochip;
generating a test mass spectrum from the application of a test serum to a test biochip;
mapping the test mass spectrum to the n-dimensional space; and
certifying that the test mass spectrum is acceptable for analysis in the bioassay if it is determined that the test mass spectrum maps to the n-dimensional space within an acceptable distance from the at least one centroid.

14. A method of determining whether mass spectral data from a test sample is acceptable for analysis in a bioassay that generates mass spectral data from the application of a sample to a biochip, comprising:
providing a location in an n-dimensional space defined by n mass spectral features of at least one centroid in the model associated with a biochip;
receiving mass spectral data associated with the test sample;
providing a location in the n-dimensional space of at least one test centroid associated with the mass spectral data from the test sample;
comparing the at least one test centroid to the at least one centroid in the model to determine the displacement in the n-dimensional space of the at least one test centroid from the at least one centroid in the model; and
certifying to a user that the mass spectral data from the test sample is acceptable for analysis in the bioassay if it is determined that the displacement is within an acceptable distance.

15. The method of claim 14, wherein the sample is serum.

16. The method of claim 14, wherein the mass spectral data is generated by surface enhanced laser desorption/ionization time of flight (SELDI-TOF) mass spectrometry.

17. The method of claim 14, wherein the biochip is selected from the group consisting of a cationic exchange biochip, an anionic exchange biochip and an immobilized metal biochip.

18. A method of determining whether mass spectral data from a test sample is acceptable for analysis in a bioassay that generates mass spectral data from a sample that is applied to a biochip, comprising:
providing a location in an n-dimensional space defined by n mass spectral features of at least one centroid in a model associated with a biochip;
receiving mass spectral data associated with the test sample;
providing a location in the n-dimensional space of at least one test centroid associated with the mass spectral data from the test sample;
comparing the at least one test centroid to the model to determine the displacement in the n-dimensional space of the at least one test centroid from the at least one centroid in the model; and
certifying to a user that the mass spectral data from the test sample is acceptable for analysis in the bioassay if it is determined that the magnitude of the displacement is acceptable.

19. The method of claim 18, wherein the test sample is accepted for analysis if the displacement of the at least one test centroid from the at least one centroid in the model is within an acceptable distance.

20. The method of claim 18, wherein the sample is serum.

21. The method of claim 18, wherein the mass spectral data is generated by surface enhanced laser desorption/ionization time of flight (SELDI-TOF) mass spectrometry.

22. A method of evaluating results for a bioassay that generates mass spectral data from the application of a serum to a biochip, comprising:
selecting a diverse group of sera, the diverse group of sera having different characteristics;
selecting a control biochip of a predetermined type;
obtaining information associated with a mass spectrum of each of the sera from the diverse group of sera using the control biochip;
generating a model based at least in p art on the spectra obtained from the diverse group of sera, the model including at least one centroid located in an n-dimensional space defined by n mass spectral features included in the model;
performing mass spectrometry on a test serum applied to a test biochip to obtain a test spectrum associated with the test serum;

mapping the test spectrum obtained from said performing to the n-dimensional space; and certifying that the test biochip is acceptable for use in the bioassay if the test spectrum maps to the n-dimensional space within an acceptable distance from the at least one centroid in the model.

23. The method of claim 22, wherein the control biochip is selected from the group consisting of a cationic exchange biochip, an anionic exchange biochip, and an immobilized metal biochip.

24. A method of evaluating results for a biological diagnostic test employing a model generated based on mass spectra obtained from application of a plurality of different sera to a preferred biochip, the model including at least one centroid located in an n-dimensional space defined by n mass spectral features included in the model, comprising:

applying a test serum to a spot on a test biochip;

performing mass spectrometry on the test serum to obtain test spectral data associated with the test serum and the test biochip; and mapping the test spectrum to the n-dimensional space; and certifying that the test biochip is acceptable for use in the biological diagnostic test if the test spectrum maps to the n-dimensional space within an acceptable distance from the at least one centroid in the model.

25. The method of claim 24, wherein the certifying includes evaluating the test spectrum in the biological diagnostic test to determine if the test serum exhibits a particular biological state.

26. The method of claim 24, wherein said performing mass spectrometry includes performing surface enhanced laser desorption/ionization time of flight (SELDI-TOF) mass spectrometry.

27. The method of claim 24, wherein said biological diagnostic test is a disease model capable of determining if the test serum exhibits a disease state associated with the disease model.

* * * * *

UNITED STATES PATENT AND TRADEMARK OFFICE
CERTIFICATE OF CORRECTION

PATENT NO. : 7,333,896 B2  Page 1 of 1
APPLICATION NO. : 10/628137
DATED : July 28, 2003
INVENTOR(S) : Ben A. Hitt et al.

It is certified that error appears in the above-identified patent and that said Letters Patent is hereby corrected as shown below:

Claim 22, Column 10, line 60, replace "p art" with -- part --.

Signed and Sealed this

Twentieth Day of January, 2009

JON W. DUDAS
*Director of the United States Patent and Trademark Office*

UNITED STATES PATENT AND TRADEMARK OFFICE
CERTIFICATE OF CORRECTION

PATENT NO. : 7,333,896 B2  Page 1 of 1
APPLICATION NO. : 10/628137
DATED : February 19, 2008
INVENTOR(S) : Ben A. Hitt et al.

It is certified that error appears in the above-identified patent and that said Letters Patent is hereby corrected as shown below:

Claim 22, Column 10, line 60, replace "p art" with -- part --.

This certificate supersedes the Certificate of Correction issued January 20, 2009.

Signed and Sealed this

Seventeenth Day of February, 2009

JOHN DOLL
*Acting Director of the United States Patent and Trademark Office*